United States Patent [19]

Kida et al.

[11] Patent Number: 4,861,597

[45] Date of Patent: Aug. 29, 1989

[54] NOVEL FUNCTIONALLIZED LIPOSOMES AND A PROCESS FOR PRODUCTION THEREOF

[75] Inventors: Masaaki Kida, Suita; Isako Kitabata, Amagasaki; Kazuhisa Kubotsu, Osaka; Yoshitsugu Sakata, Otsu, all of Japan

[73] Assignee: Wako Pure Chemical Industries, Ltd., Osaka, Japan

[21] Appl. No.: 51,349

[22] Filed: May 19, 1987

[30] Foreign Application Priority Data

May 20, 1986 [JP] Japan ................................. 61-115405
Oct. 13, 1986 [JP] Japan ................................. 61-242746

[51] Int. Cl.$^4$ ............................................. A61K 37/22
[52] U.S. Cl. ............................. 424/450; 428/402.21; 428/402.24; 424/85.9; 264/4.1; 264/4.33; 264/4.32; 264/4.3
[58] Field of Search ..................... 424/450, 85; 428/402.21, 402.24; 204/4.1, 4.33, 4.32, 4.3

[56] References Cited

U.S. PATENT DOCUMENTS 4,565,696 1/1986 Heath et al. .

FOREIGN PATENT DOCUMENTS

| 0-007714 | 2/1980 | European Pat. Off. . |
| 0-047480 | 3/1982 | European Pat. Off. . |
| 0-155625 | 3/1984 | European Pat. Off. . |
| 01-80980 | 5/1986 | European Pat. Off. . |
| 2-597345 | 10/1987 | France . |
| 60-117159 | 6/1985 | Japan . |

OTHER PUBLICATIONS

Bangham et al, J. Mol. Viol., 13, 238 (1965).
J. H. Fendler, "Membrane Mimertio Chemistry", John Wiley & Sons, N.Y. (1982).
C. Hudng et al, Biochemistry, 8, 344 (1969).
F. Szoka et al, Proc. Natl. Acad., Sci., U.S.A., 75, 4194 (1978).
S. Batzri et al, Biochem. Biophs. Acta, 298, 1015 (1973).
D. Deamer et al, Biochim., Biophys., Acta., 443, 629 (1976).
J. R. Slack et al, Biochim. Biophys. Acta., 323,547 (1973).
F. Szoka et al, Ann. Rev. Biophys. Bioeng., 9,467 (1980).
Biochemical et Biophysical Acta., 812, 1116 (1985).
Biochemical et Biophysical Acta., 640, 66 (1981).
Journal of Immunological Method, 75, 351 (1984).
Biochemical & Biophysical Research Communications, 117, 399 (1983).
Biochemical and Biophysical Research Communications, 89, 1114 (1979).
Liposome Technology, 155 (1983), CRC Press.
Partial translation of FR-A-2597345.
Partial translation of EP-A-0155625.

*Primary Examiner*—William R. Dixon, Jr.
*Assistant Examiner*—Karl Group
*Attorney, Agent, or Firm*—Armstrong, Nikaido Marmelstein Kubovcik & Murray

[57] ABSTRACT

Novel functionallized liposomes containing a high-molecular-weight amphiphilic compound such as LPS etc. as one of matrix material have a very high encapsulation efficiency and readily undergo lysis. Moreover, antigen, antibody, etc. can be immobilized on the liposomes efficiently with a sufficient binding rate by using the amphiphilic compound as a spacer.

17 Claims, 4 Drawing Sheets

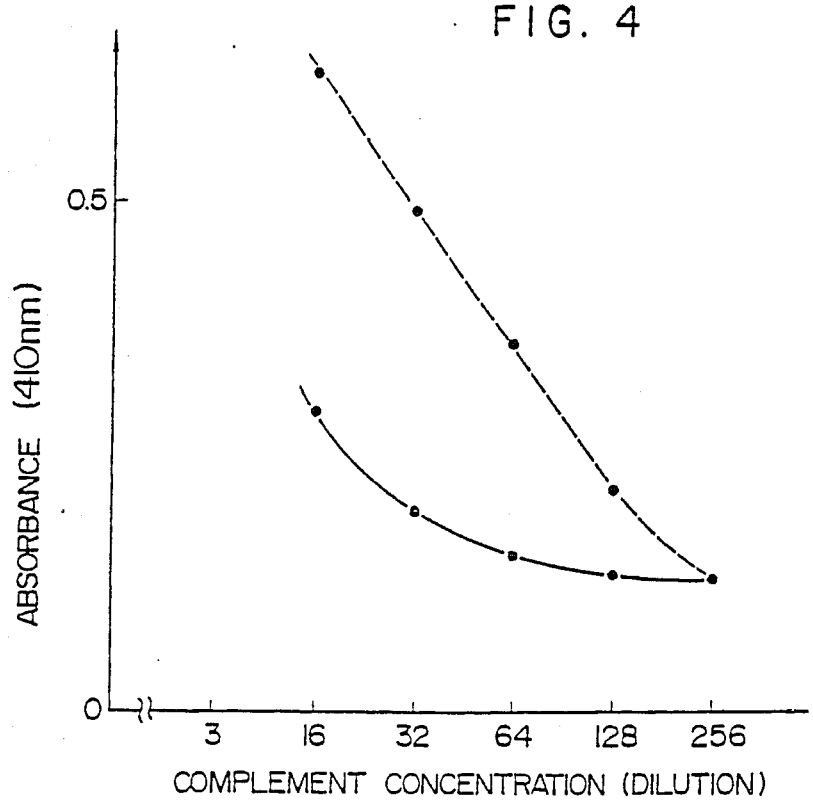

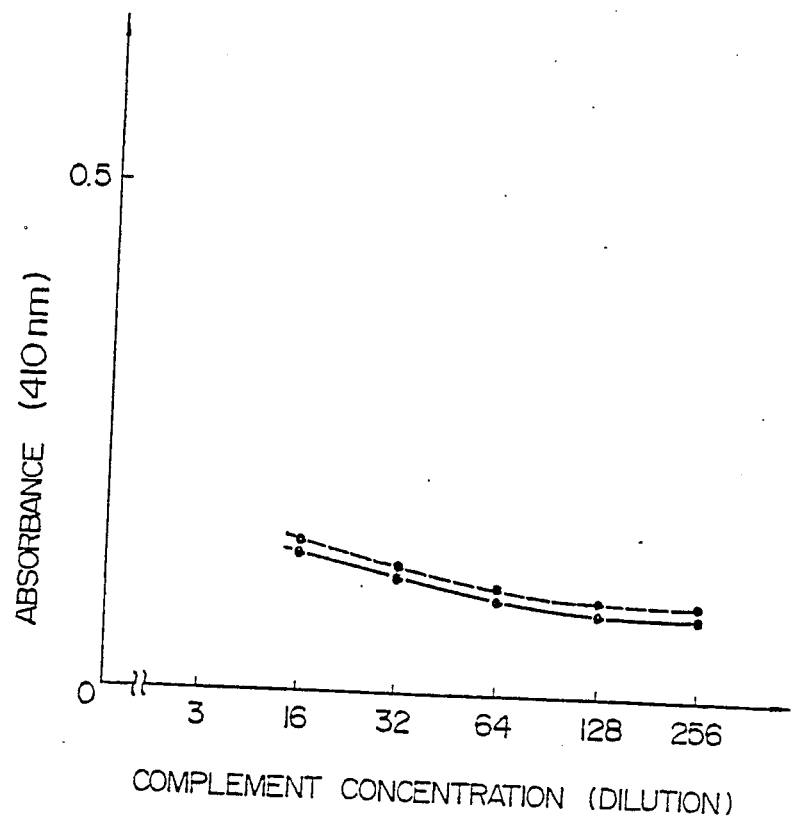

NOVEL FUNCTIONALLIZED LIPOSOMES AND A PROCESS FOR PRODUCTION THEREOF

BACKGROUND OF THE INVENTION

This invention relates to novel functionallized liposomes used in the medical fields such as clinical examinations, diagnosis, remedy, etc. and a process for production thereof.

More particularly, this invention relates to novel functionallized liposomes comprising a high-molecular-weight amphiphilic compound as one of matrix material, and a process for production thereof. The functionallized liposomes of this invention have a very high encapsulation efficiency, and make it possible to immobilize immunological substances, biological active substances, etc. on liposomes efficiently with a sufficient binding rate without injuring the liposome.

Since Bangham et al. found that when phospholipids which are surfactants derived from biomembranes were suspended in water, closed vesicles composed of lipid bilayers were formed (J. Mol. Biol. 13,238 (1965)), these vesicles have been called liposomes and in recent years, their preparation method and application in various fields have energetically been investigated. In addition, it has recently also been found that besides phospholipids, highly molecular-designed artificial synthetic lipids (amphiphilic substances having molecular weight of about 1,000) form vesicles like liposomes (J. H. Fendler, "Membrane Mimetic Chemistry", John Wiley & Sons, N.Y., (1982)). Liposomes are noted very widely in the fields of clinical examinations, diagnosis, medicines, etc. because of their biocompatibility, not only as mere models of functions and structural characteristics of cells but also as artificial erythrocytes, a means for introducing genetic information into protoplasts in genetic engineering, carriers for immobilizing enzymes, and drug delivery systems for developing and improving remedies for cancer and other incurable diseases.

As conventional methods for preparing encapsulating liposomes, there have been reported many methods such as the most fundamental method comprising formation of a lipid thin film, followed by treatment by vortexing (A. D. Bangham et al, J. Mol. Biol., 13, 238 (1965)), sonication or the like (C. Hudng et al, Biochemistry, 8, 344 (1969)), the reverse-phase evaporation method (REV method) using organic solvents (F. Szoka et al, Proc. Natl. Acad. Sci., U.S.A., 75, 4194 (1978)), the ethanol infusion method (S. Batzri et al, Biochem. Biophs. Acta., 298, 1015 (1973)), the ether infusion method (D. Deamer et al, Biochim. Biophys. Acta., 443, 629 (1976)), and methods using surfactants (J. R. Slack et al, Biochim. Biophys. Acta., 323, 547 (1973)). Various types of liposomes can be prepared by these preparation methods. Liposomes range in size widely from 0.02 to 10 $\mu$m diameter, and according to their size and structure, they are usually roughly divided into three types, namely, multilamellar vesicles (abbreviated as MLVs, 0.3 to 10 $\mu$m in diameter), small unilamellar vesicles (abbreviated as SUVs, 0.025 to 0.1 $\mu$m in diameter), and large unilamellar vesicles (abbreviated as LUV, 0.2 to 2.0 $\mu$m in diameter) (F. Szoka et al, Ann. Rev. Biophys. Bioeng., 9, 467 (1980)). In addition to them, there are oligolamellar vesicles, and liposomes obtained particularly by the REV method are separately dealt with as reverse-phase evaporation vesicles (abbreviated as REVs) in some cases. The encapsulation efficiency indicated the rate of retention of encapsulated substances in liposomes, and is defined as the volume of water held per mole of lipid. This value varies depending on the kind of liposome, and now it is considered that liposomes prepared by the REV method have the highest encapsulation efficiency and that LUV is the second to be able to encapsulate proteins and nucleic acids. However, any of these liposomes obtained by conventional preparation methods are not always sufficient in captured volume for encapsulating high-molecular-weight substances such as enzyme proteins, and the advent of liposomes having a larger captured volume and a higher encapsulation efficiency has been eagerly waited for in consideration of application in the field of medical treatment, diagnosis, clinical examinations, etc., for example, encapsulation of expensive drugs in liposomes and preparation of highly sensitive diagnostic pharmaceutical compositions.

On the other hand, when used for clinical examinations or as diagnostic drugs or drug delivery systems for curative drugs for cancer and other incurable diseases, liposomes are used usually after immobilization thereon of antigen, antibody, other proteins, etc.

As methods for immobilizing antigen, antibody, other proteins, etc. on liposomes, there have so far been known the following methods (i) to (iv).

(i) A method which comprises introducing a hydrophobic group into a protein to be immobilized on liposomes, thereby imparting thereto affinity for liposomes, and then incorporating the thus treated protein into separately prepared liposomes (Biochemical et Biophysical Acta., 812, 116 (1985), etc.).

(ii) A method which comprises mixing a substance having a chemically modifiable group, e.g., ganglioside (molecular weight: about 2,000) which is a low-molecular-weight glycolipid, previously at the time of liposome preparation, oxidizing its saccharide moiety with an oxidizing agent to form an aldehyde group, reacting the aldehyde group with the amino group of protein to form a Schiff base, and thereby combining liposome with the protein (Biochemical et Biophysical Acta, 640, 66 (1981), etc.).

(iii) A method which comprises mixing a lipid having a functional group reactive to SH group at the time of liposome preparation as in (ii) above, and reacting with protein separately modified with a sulfhydrylating agent to incorporate the same (Journal of Immunological Method, 75, 351 (1984); Biochemical and Biophysical Research Communications, 117, 399 (1983); Japanese Patent Application Kokai (Laid-Open) No. 117159/85, etc.).

(iv) A method which comprises binding the respective functional groups of liposomes and protein to each other by use of a cross-linking agent, a condensing agent or the like without any previous treatment of the liposomes and the proteins (Biochemical and Biophysical Research Communications, 89, 1114 (1979); Liposome Technology, 155 (1983), CRC Press, etc.).

However, in all these methods protein such as antigen or antibody is immobilized by reacting near the surface of liposomes, and therefore the membrane structure is very liable to be injured at the time of reaction and the binding rate of protein is not always sufficient, resulting in low efficiency, because of the steric hindrance of liposome matrix.

In general, when liposomes on which antibody or antigen is immobilized are used, for example, for clinical examinations or in diagnostic drugs, liposomes which readily undergo immunolysis by the action of complement, etc. after antigen-antibody reaction are preferred and hence the development of liposomes which are susceptible to immunolysis is desired.

SUMMARY OF THE INVENTION

An object of this invention is to provide functionalized liposomes having a very high encapsulation efficiency which can be suitably used in the various medical fields such as clinical examinations, diagnosis, remedy, etc.

Another object of this invention is to provide liposomes on which immunological substances, physically active substances, etc. can be immobilized efficiently with a sufficient binding rate without injuring the liposome, or functionallized liposomes having these substances immobilized thereon efficiently with a sufficient binding rate.

Further another object of this invention is to provide functionallized liposomes which readily undergo immunolysis, can be used for immunoassay as stable immunoliposomes, and are very useful for clinical examinations, diagnostic drugs, etc.

Still another object of this invention is to provide functionallized liposomes excellent in storage stability.

Still another object of this invention is to provide a process for producing liposomes which makes it possible to immobilize immunological substances, physiologically active substances, etc. on liposomes encapsulating useful substances such as enzymes, fluorescent substances, etc., efficiently with a sufficient binding rate without injuring the liposomes (namely, without leakage of the encapsulated substances).

According to this invention, there are provided functionallized liposomes comprising an amphiphilic compound having a molecular weight of about 5,000 to about 30,000 as one of matrix material, and a process for producing functionallized liposomes, characterized by forming the same in the presence of an amphiphilic compound having a molecular weight of about 5,000 to about 30,000 as one of matrix material.

BRIEF DESCRIPTION OF THE DRAWINGS

FIG. 4 shows the results of immunolysis in Example 14. FIG. 5 shows the results of immunolysis in comparative Example 1. In both FIG. 4 and FIG. 5, the axis of ordinate refers to absorbance at 410 nm and the axis of abscissa to the concentration of complement, and the solid line—shows the results obtained in the case of acting complement alone on liposomes having IgG attached thereto and the broken line . . . the results obtained in the case of acting the complement and anti-IgG antibody (antiserum) on liposomes having IgG attached thereto.

DETAILED DESCRIPTION OF THE INVENTION

Figure 1:
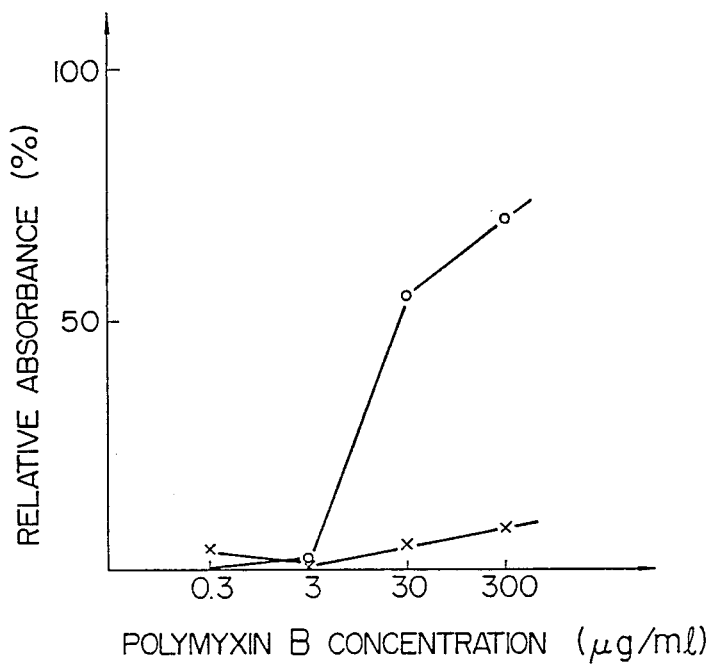
FIG. 1 shows the measurement results obtained in Example 10 in investigating the lysis behavior of the liposomes of this invention by use of polymyxin B (shown by -O- ) and those obtained for liposomes for comparison prepared by a conventional method (shown by -X-); the axis of abscissa refers to polymyxin concentration ($\mu$g/ml) and the axis of ordinate to relative absorbance (%) determined by taking the value (absorbance) for lysis by Briji 58 as 100.

In this invention, an amphiphilic compound having a molecular weight of about 5,000 to about 30,000 is used as one of matrix material for liposomes. As such an amphiphilic compound, there are preferably exemplified, for example, lipopolysaccharides (hereinafter referred to as LPS), lipopolysaccharide-like compounds, natural polypeptides having a hydrophobic group by nature, natural polypeptides having a hydrophobic group introduced thereinto, hydrophilic synthetic polypeptides having a hydrophobic group, and hydrophilic polymers whose ends have been made hydrophobic.

The LPS used in this invention is that derived from gram-negative bacteria such as *Escherichia coli*, lactic acid bacteria, etc. and those derived from *E. coli* are usually preferably used, but the LPS is not limited thereto and those obtained by treatment by the Wastphal method, and the like also can sufficiently be used. The LPS-like compounds according to this invention are compounds obtained by subjecting LPS to chemical modification, and includes, for example, compounds obtained by oxidation of the saccharide chain portion, compounds obtained by chemical treatment such as acetylation, succinylation, phthalylation or the like of the saccharide chain portion, etc.

The natural polypeptides having a hydrophobic group by nature include, for example, polypeptide having a signal peptide. The natural polypeptides having a hydrophobic group introduced thereinto include, for example, those obtained by introducing a hydrophobic group into the amino group or carboxyl group of insulin. The hydrophilic synthetic polypeptides having a hydrophobic group include, for example, poly(glutamic acid) and poly(lysine) bound to long alkyl groups.

In this invention, liposomes having a very high encapsulation efficiency can be obtained particularly when LPS or a LPS-like compound is used as the amphiphilic compound. Between them LPS is particularly preferred. Particularly when there is used LPS, LPS-like compound, a natural polypeptide having a hydrophobic group by nature, a natural polypeptide having a hydrophobic group introduced thereinto, a hydrophilic synthetic polypeptide having a hydrophobic group, or a hydrophilic polymer whose ends have been made hydrophobic, immunological substances or physiologically active substances can be immobilized on the resulting liposomes efficiently with a sufficient binding rate without injuring the liposome. Among them, LPS is particularly preferred.

As constitutive materials for the liposomes of this invention, there can be used all the constitutive material usually used in known methods for producing liposomes, for example, phospholipids such as natural lecithins (e.g., egg yolk lecithin, soybean lecithin, etc.), dipalmitoyl phosphatidyl choline (DPPC), dimyristoyl phosphatidyl choline (DMPC), distearoyl phosphatidyl choline (DSPC), dioleoyl phosphatidyl choline (DOPC), dimyristoyl phosphatidyl ethanolamine (DMPE), dipalmitoyl phosphatidyl glycerol (DPPG), dimyristoyl phosphatidic acid (DMPA), and the like alone or in combination of two or more thereof, and mixtures thereof with cholesterols, etc.

The functionallized liposomes of this invention prepared by any preparation method have a much higher encapsulation efficiency for a substance to be encapsulated than do conventional liposomes, and can efficiently encapsulate either various high-molecular-weight compounds or biochemical high-molecular-weight substances. As compounds which the liposomes of this invention can encapsulate, there may be exemplified all the substances which can be encapsulated in known liposomes, for example, either biochemical high-molecular-weight substances such as enzymes (e.g., alkaline phosphatase), genes, nucleic acids, polynucleotides, hormones, immunoglobulins, etc. or low-molecular weight compounds such as various drugs, antibiotics, dyes, fluorescent substances, luminous compounds, etc.

Like known liposomes, the liposomes of this invention permit immobilization of immunological substances or physiologically active substances on their membranes. The immunological substances which can be immobilized on the liposomes of this invention include, for example, low-molecular-weight antigens such as glycolipids, etc.; protein antigens such as tumor markers (e.g., α-fetoprotein, carcinoembryonic antigen (CEA), basic fetoprotein (BFP), pancreatocarcinoembryonic antigen (POA), etc.), antigenic proteins (e.g., C-reactive protein (CRP), etc.), and immunoglobulins (e.g., IgA, IgE, IgG, IgM, etc.); low-molecular-weight haptenic antigens obtained by combining various drugs with proteins and the like; and antibodies to these antigens.

The physiologically active substances include, for example, hormones such as insulin, human chorionic gonadotropin (hCG), etc., and various drugs such as anticancer agents, etc.

As a method for producing the liposomes of this invention, there may be exemplified all the per se well-known methods for producing liposomes, for example, heretofore well known methods such as the vortexing method, sonication method, surfactant method, reverse-phase evaporation method (REV method), ethanol infusion method, ether infusion method, pre-vesical method, French press extrusion method, $Ca^{2+}$ fusion method, annealing method, freeze-thaw-fusion method, W/O/W emulsion method, etc.; methods such as the stable plurilamellar vesicle method (SPLV method) recently reported by S. M. Gruner et al. (Biochemistry, 24, 2833 (1985)); and methods for preparing liposomes called "giant liposomes" which have a large captured volume.

That is to say, it is sufficient that the functionallized liposomes of this invention are produced according to these per se well-known methods or other methods for producing liposomes, except that the liposomes are formed in the presence of an amphiphilic compound having a molecular weight of about 5,000 to about 30,000 as one of the matrix material.

For encapsulating a biochemical high-molecular-weight substance or a low-molecular-weight compound in the functionallized liposomes of this invention, the presence of the biochemical high-molecular-weight substance or the low-molecular substance in a suitable step in the production of the functionallized liposomes is sufficient.

As a method for immobilizing an immunoreactive substance or a physiologically active substance on the liposomes, there may be exemplified methods utilizing all the per se well-known methods (K. Peters et al, Ann. Rev. Biochem., 46 523 (1977); F. Wold et al, Methods Enzymol., 258 585 (1972)), for example, a method comprising activating the functional group of an amphiphilic compound having a molecular weight of about 5,000 to about 30,000 used as one of matrix material for liposomes and incorporated into the liposomes, and thereby reacting the amphiphilic compound with substance to be immobilized; a method comprising binding a immunological substance or a physiologically active substance through the amphiphilic compound by use of a cross-linking agent such as a univalent cross-linking agent, a divalent cross-linking agent or the like; a method using a binder and binding substance to be immobilized through the amphiphilic compound.

In this invention, the liposomes contain an amphiphilic compound having a molecular weight of about 5,000 to about 30,000 incorporated thereinto as one of matrix material, and when an immunological substance, a physiologically active substance or the like is bound to the liposomes through the amphiphilic compound, the amphiphilic compound functions as a spacer and immobilization reaction is carried out necessarily at a suitable distance from the liposome surface, so that only slight disorder is caused on the membrane surface, resulting in stable and efficient immobilization.

In the liposome of this invention, it is also possible to conduct the immobilization of immunological substances or physiologically active substances by a conventional cross-linking method, lipid activation method or the like without the aid of the above-mentioned amphiphilic compound (H. Endoh et al, J. Immunol. Method, 36, 185 (1980); ibid, 44, 79 (1981); E. J. Martin, J. Biol. Chem., 257, 286 (1982)).

Such a cross-linking method comprises first reacting a conventional cross-linking agent with a desired lipid used for liposome production in a solvent to introduce a functional group capable of linking to an antigen, an antibody or the like to be immobilized on liposomes into the lipid molecules, preparing liposomes by use of the functional lipid thus obtained, and immobilizing the antigen, antibody or the like on the liposomes through the functional group derived from the functional lipid.

The lipid activation method comprises first binding a lipid to an antigen or an antibody by use of a cross-linking agent or an activating agent for lipid, and preparing liposomes by use of the combined product thus obtained.

A method for producing the functionallized liposomes of this invention is explained below in detail by taking the case of the surfactant method.

First, such phospholipids and cholesterols described above are dissolved in an organic solvent (e.g., chloroform, an ether, an alcohol, etc.), and the resulting solution is concentrated to dryness under reduced pressure and then sufficiently dried under reduced pressure in a desiccator. Subsequently, an aqueous surfactant solution (10 mM to 500 mM) is added to the lipid film thus formed and the film is uniformly dispersed thereinto. The surfactant used here includes, for example, those heretofore often used such as cholic acid, Tritons, octyl glucoside, etc., though surfactants having a high critical micelle concentration (CMC) such as octyl glucoside and the like are preferred. Next, LPS, an LPS-like compound or the like which is the key to the method of this invention is added in powder form as it is or in solution, followed by adding thereto a solution of a desired substance to be encapsulated (e.g., an enzyme), and the resulting mixture is sufficiently stirred. It is most preferable to remove the surfactant immediately after the stirring, and a method for the removal includes per se well-known methods such as dialysis, gel filtration, absorption on resin, etc. As to the treatment conditions, the treatment time is 1 to 24 hours, and treatment temperature may be properly selected in the range of about 0° to about 70° C. though it is somewhat varied depending on the constitutive material for liposomes, the properties (stability, etc.) of the substance to be encapsulated, etc. In order to remove LPS or the like and the substance which have not been encapsulated, it is recommendable to select a removal method from the above-mentioned method depending on the kind of the substance to be encapsulated, as follows. When the substance to be encapsulated is a low-molecular-weight substance, the removal is carried out by dialysis, gel filtration through Sephadex G-50, etc. and when it is a high-molecular-weight substance, the removal is carried out by gel filtration through Sepharose 4B, centrifugation, etc. The liposomes thus obtained are used or stored after being concentrated by ultrafiltration or the like so as to have a predetermined concentration. For making the sizes of the liposomes uniform, a method using a generally used polycarbonate membrane may be employed, though a gel filtration (using, for example, Sephacryl S-1000) is also effective.

Also when the functionallized liposomes of this invention are produced by a method other than the surfactant method, it is sufficient that they are produced similarly according to a per se well-known method or other methods for producing liposomes, except for the presence of an amphiphilic compound such as LPS, an LPS-like compound or the like.

The thus obtained functionallized liposomes encapsulating an enzyme or the like of this invention have a transparent appearance with substantially no turbidity, while liposomes prepared by a conventional method have a considerable turbidity. Moreover, they are excellent in storage stability. The recovery of phospholipid for the liposomes obtained by the method of this invention is usually about 60 to about 70% and is generally high than that for liposomes obtained by a conventional method. The capture volume of the functionallized liposomes of this invention is about 2 to about 20 times that of liposomes obtained by a conventional method, for example, in the case of alkaline phosphatase (abbreviated as AP). The capture volume is greatly affected primarily by the proportion of LPS (or an LPS-like compound or the like) present in the formation of the liposomes, though it somewhat varies depending also on the preparation method and the preparation conditions. For example, when the concentration (amount) of LPS range from 1 to 5 mg/ml per 6.4 mg/ml of egg yolk lecithin, the efficiency is high, but when it is less than 1 mg/ml or more than 5 mg/ml, the efficiency tends to be lowered in some cases.

Therefore, in this invention, the using amount of the amphiphilic compound having a molecular weight of about 5,000 to about 30,000 is usually preferably to 0.01–2 w/w % particularly preferably to 0.05–1 w/w % relative to the phospholipid which is a constitutive material for the liposomes.

Needless to say, the encapsulation efficiency depends also on the charging amount of AP at the time of preparation. For example, the encapsulation efficiency is highest when the amount of AP is more than 300 U per 9.5 mg of egg yolk lecithin.

In the case of the LPS-liposomes encapsulating AP, the activity is entirely stable usually for about 4 to about 5 months, though it varies somewhat depending on storage temperature (usually 4° to 37° C.), liposome concentration, etc.

The functionallized liposomes encapsulating AP of this invention have very interesting properties different from those of conventional liposomes containing no LPS. That is to say, these liposomes generally undergo lysis of a surfactant, resulting in recovery of the activity of encapsulated enzyme, but when a substance having a high affinity for LPS such as polymyxin is used, conventional liposomes hardly undergo lysis and only the liposomes containing LPS of this invention (LPS-liposomes) undergo lysis specifically.

Next, the details of the immobilization method of this invention is explained below by taking the case where IgG is immobilized using LPS as an amphiphilic compound.

From the LPS-liposomes containing LPS obtained by the above-mentioned preparation method, there is obtained a suspension of the LPS-liposomes (usually a dispersion in a buffer solution such as a "Good" buffer (HEPES, PIPES, MES, etc., Good et al, *Biochem,* 5, 467, (1966) and *Method Enzymol.* 24, Part B, 53 (1968)), Tris buffer, carbonate buffer, etc.). Subsequently, a solution of an oxidizing agent (e.g., potassium periodate, sodium metaperiodate, etc.) in a buffer solution is added thereto, and the resulting mixture is subjected to reaction with stirring at room temperature for 1 to several hours to oxidize the saccharide chain portion of LPS, whereby an aldehyde group is formed. The reaction mixture is centrifuged and the supernatant is removed, after which the residue is resuspended in a suitable buffer solution. Then, a solution of IgG in a buffer solution is added and the resulting mixture is subjected to reaction with stirring at room temperature for several hours to form a Schiff base. Subsequently, a solution of a reducing agent (e.g., sodium borohydride, lithium aluminum hydride, etc.) in a buffer solution is added, and the resulting mixture is subjected to reaction with stirring at room temperature for 1 to several hours and then centrifuged, after which the supernatant is removed to obtain liposomes having IgG attached thereto, in high yield.

As described above in detail, according to this invention, there can be obtained liposomes which have a high encapsulation efficiency, readily undergo lysis, and have an excellent storage stability. Furthermore, according to this invention, immunological substances, physiologically active substances, etc. can very efficiently be immobilized on liposomes encapsulating a useful substance, without injuring the liposomes.

According to electron microscopic observation, light microscopic observation, the measurement of particle size distribution (by light scattering), etc., there may be frequent cases wherein the liposomes of this invention are clearly different also in shape from liposomes obtained by a conventional method and their size is larger than that of the latter. Furthermore, the liposomes of this invention hardly aggregate and are more stable.

Examples and Referential Examples are given below, but are not by way of limitation but by way of illustration.

EXAMPLE 1

Preparation of LPS-liposomes (surfactant method using egg yolk lecithin)

In a flask were placed 0.65 ml of a 1.47 wt % solution of egg yolk lecithin in chloroform and 0.22 ml of a 20 mM solution of cholesterol in chloroform, and the solvent was removed by distillation by means of a rotary evaporator to form a thin film on the interior surface of the flask. The thin film was dried in vacuo in a desiccator for 1 to 2 hours, after which 1.5 ml of a 200 mM aqueous octyl glucoside solution was added and the resulting mixture was stirred in a Vortex mixer until uniform dispersion was achieved. Subsequently, 300 μl of an aqueous alkaline phosphates (AP) solution (1000 U/1 ml H$_2$O) and 3 mg of LPS having average molecular weight of 20,000 were added and the resulting mixture was stirred for another 5 minutes. This mixture was placed in a dialyzing tube and dialyzed about overnight against 2 liters of 50 mM Tris buffer (pH 7.8), after which the liposome suspension thus obtained was applied to a Sepharose 4B column (1.5×25 cm) and a dispersion of desired LPS-liposomes was obtained by gel filtration.

EXAMPLE 2

Preparation of LPS-liposomes (REV method using DPPC)

A solution of 1.5 mg of LPS having average molecular weight of 20,000 in chloroform was added to a mixed lipid system (solvent: chloroform) of 6.5 μmol of dipalmitoyl phosphatidyl choline (DPPC), 0.65 μmol of dipalmitoyl phosphatidyl glycerol (DPPG), 6.5 μmol of cholesterol and 0.325 μmol of dithiopyridyl dipalmitoyl phosphatidyl ethanolamine (DTP-DPPE), and the resulting mixture was concentrated to dryness under reduced pressure and then sufficiently dried. To the residue were added 0.5 ml of chloroform and 0.5 ml of ethyl ether to dissolve the residue, after which an AP solution [160 U in HEPES (N-2-hydroxyethylpiperazine-N'-2-ethanesulfonic acid) buffer] was added and the resulting mixture was sufficiently stirred to obtain an emulsion. After the solvent was removed by distillation by means of a rotary evaporator under reduced pressure at about 45° C., HEPES buffer was further added, followed by vigorous stirring. The suspension thus obtained was passed through a polycarbonate membrane (1.0 μm) and then ultracentrifuged (34,000 r.p.m., 75,000 xg 4° C.) and the supernatant was removed, after which the pellet was dispersed into 2 ml of HEPES buffer to obtain LPS-liposomes.

EXAMPLE 3

Preparation of LPS-liposomes (SPLV method using DPPC)

An AP solution (160 U in HEPES buffer) was added to a solution of the same mixed lipid system as in the above REV method in chloroform/ether to obtain an emulsion, after which the solvent was removed by distillation in a bath type ultrasonic washer in a N$_2$ stream at about 45° C. for about 5 minutes. Subsequently, HEPES buffer was added to the residue, followed by vigorous stirring, and the suspension thus obtained was centrifuged (12,000 r.p.m., 9,000 xg; 4° C.) and the supernatant was removed, after which the pellet was redispersed into HEPES buffer to obtain LPS-liposomes.

EXAMPLE 4

Preparation of LPS-liposomes (Surfactant method using DPPC)

Into a round bottom flask were placed the solution (2 ml) of DPPC (20 mM) in chloroform and the solution (2 ml) of cholesterol (20 mM) in chloroform, and the solvent was removed by a rotary evaporator to form a thin film on the interior surface of the flask. The thin film was dried in vacuo in a desiccator for 1-2 hours, to which 0.6 ml of 200 mM aqueous octyl glucoside solution containing LPS having average molecular weight of 20,000 (6.6 mg/ml) was added and the mixture was stirred in a Vortex mixer until uniform dispersion was achieved. Subsequently, 250 μl of an aqueous alkaline phosphatase (AP) solution (2000 U/ml) was added the resulting mixture was stirred for another 5 minutes. This mixture was placed in flow type dialyzing for apparatus and dialyzed about 2 hours thermocontrolled at 50° C. in a water bath against HEPES buffer (10 mM, pH 7.4). The liposome suspension thus obtained was isolated by ultracentrifugation (34000 rpm. 4° C.), and the supernatant fluid was removed to separate the unencapsulated AP. The pellets were resuspended with HEPES buffer and the process was repeated more 3 times, to obtain LPS-liposomes.

EXAMPLE 5

Preparation of LPS-liposomes (REV method using egg yolk lecithin)

The LPS-liposomes were obtained in the same manner as in Example 2 except that 4.7 mg of egg yolk lecithin was used in place of 0.65 μmol of DPPC.

EXAMPLE 6

Preparation of LPS-liposomes (SPLV method using egg yolk lecithin)

The LPS-liposomes were obtained in the same manner as in Example 3 except that 4.7 mg of egg yolk lecitin was used in place of 0.65 μmol of DPPC.

EXAMPLE 7

Preparation of LPS-liposome (Vortex mixing method using DPPC)

A powder of 1.6 mg of LPS having average molecular weight of 20,000 was added to a mixed lipid system [solvent; chloroform, lipid; DPPC (8 μmol), Dicethylphosphate (DCP) (1.76 μmol), Cholesterol (8 μmol)], and the resulting mixture was concentrated to dryness under reduced pressure and then sufficiently dried. To the residue were added 160 μl of AP buffer solution [160 U, Tris-buffer (50 mM), pH 7.8] and stirred vigorously until uniformly suspended. The suspension thus obtained was passed through a polycarbonate membrane and then centrifuged (15000 rpm, 14,000 xg 4° C.) and the supernatant was removed, after which the pellet was redispersed into 2 ml of Tris-buffer to obtain LPS-liposome.

EXAMPLE 8

Preparation of LPS-liposomes (Vortex mixing method using egg yolk lecithin)

The LPS-liposomes were obtained in the same manner as in Example 7 except that 11.8 mg of egg yolk lecithin was used in place of 8 μmol of DPPC.

EXAMPLE 9

Determination of encapsulated amount (AP activity) in liposomes from lysis by surfactant (Briji 58)

Briji 58 (a 1% solution) was added to 10 μl of each of the liposome dispersions of this invention obtained by various preparation methods, and the resulting mixture was incubated at 37° C. for 30 minutes, after which 2 ml of a 2 mM p-nitrophenylphosphate solution was added as a chromogenic substrate, and the mixture thus obtained was incubated for another 30 minutes. Then, 1 ml of 0.5N NaOH was added and absorbance at 410 nm was measured, whereby the amount of AP encapsulated was determined.

The results obtained are shown in Tables 1a and 1b. For comparison, in Tables 1a and 1b are also shown the results for liposomes prepared by the same method as for the liposomes of this invention, except that no LPS was added (namely, a conventional method).

TABLE 1a

The amount of AP encapsulated in LPS-liposomes prepared using egg yolk lecithin (determined by Briji 58 lysis assay)

| Preparation method | Conventional method | LPS method |
| --- | --- | --- |
| Surfactant method | 100 | 441 |
| Vortexing method | 30 | 104 |
| REV method | 1290 | 2670 |
| SPLV method | 670 | 1070 |

TABLE 1b

The amount of AP encapsulated in LPS-liposomes prepared using DPPC (determined by Briji 58 lysis assay)

| Preparation method | Conventional method | LPS method |
| --- | --- | --- |
| Surfactant method | 100 | 2490 |
| Vortexing method | 690 | 1033 |
| REV method | 18400 | 38300 |
| SPLV method | 9670 | 15300 |

The numerical values in Tables 1a and 1b shows relative values of AP activity per mole of phospholipid determined by taking the AP activity in the case of surfactant method according to a conventional method as 100.

As is evident from Tables 1a and 1b, all the liposomes (LPS-liposomes) of this invention show a much larger amount of AP encapsulated than do the liposomes obtained by a conventional method.

EXAMPLE 10

Lysis behavior of LPS-liposomes by polymyxin B

To 10 μl of a liposome (LPS-liposome) dispersion of this invention obtained by the surfactant method using egg yolk lecithin was added 100 μl of a polymyxin B solution having a predetermined concentration, followed by adding thereto 3 ml of 2 mM p-nitrophenylphosphate, and the resulting mixture was incubated at 37° C. for 30 minutes, after which absorbance at 410 nm was measured, whereby the lysis behavior was investigated.

The results obtained are shown in FIG. 1 (shown by -O-). For comparison, the results of the same measurement as above for liposomes obtained by a conventional method are also shown in FIG. 1 (shown by -X-). The axis of ordinate in FIG. 1 refers to the magnitude of lysis at the corresponding polymyxin concentration in terms of relative values determined by taking the value (absorbance) for lysis by Briji 58 as 100.

It can be seen from FIG. 1, lysis that by polymyxin B occurs specifically only in the liposomes containing LPS of this invention.

EXAMPLE 11

Preparation of LPS-liposomes having IgG attached thereto (by a conventional cross-linking method)

Egg yolk lecithin (a solution in chloroform), cholesterol (a solution in chloroform) and DTP-DPPE A (solution in chloroform) were mixed in the ratio of 13:4.4:0.1 by mol, and the solvent was removed by distillation to form a thin film. This lipid film was dried under reduced pressure, and 1.5 ml of a 200 mM aqueous octyl glucoside solution, 3 mg of LPS having average molecular weight of 20,000 and 180 μl of an aqueous AP solution (1000 U/1 ml $H_2O$) were added to dissolve the lipid film, after which the resulting solution was dialyzed overnight against 50 mM Tris-HCl buffer containing 0.15M NaCl (pH 7.8). The suspension thus obtained was purified by use of Sepharose 4B to obtain liposomes encapsulating AP and having DTP group as a functional group capable of linking to antigen (IgG), at the membrane surface.

Separately, 5 mg of human IgG was dissolved in 2 ml of 0.01M HEPES buffer containing 0.85% NaCl (pH 7.4), and 10 μl of 10 mM N-succinimidyl-3-(2-pyridyldithio)propionate (SPDP) was added to react therewith. Then, the reaction solution was applied to gel filtration through Sephadex G-25 (0.1M acetate buffer containing 0.15M NaCl, pH 4.5), after which 30 mg of dithiothreitol (DTT) was added to 2 ml of the protein fraction thus obtained and the reaction was carried out. The reaction solution thus obtained was applied to Sephadex G-25 gel column equilibrated with 0.01M HEPES buffer, whereby an SPDP-modified IgG fraction was obtained.

The SPDP-modified IgG thus obtained and an equal amount of the liposomes previously obtained were mixed and then reacted overnight at room temperature. After completion of the reaction, a liposome fraction was separated by use of Sephadex 4B to obtain an IgG-attached LPS-liposome dispersion.

REFERENTIAL EXAMPLE 1

Quantitation of IgG using IgG-attached LPS-liposomes

Human IgG was quantitated using the IgG-attached LPS-liposomes obtained in Example 11. In a test tube were placed 20 μl of the IgG-attached liposomes, 200 μl of anti-IgG serum, 20 μl of each of human IgG solutions different in concentration, and 200 μl of guinea pig serum complement (1 $CH_{50}$), and the reaction was carried out at 37° C. for 30 minutes. Next, 400 μl of 20 mM p-nitrophenylphosphate was added, and the resulting mixture was subjected to reaction at 37° C. for 30 minutes, after which 1.5 ml of 0.1N NaOH was added to stop the reaction and absorbance at 410 nm was measured.

Figure 2:
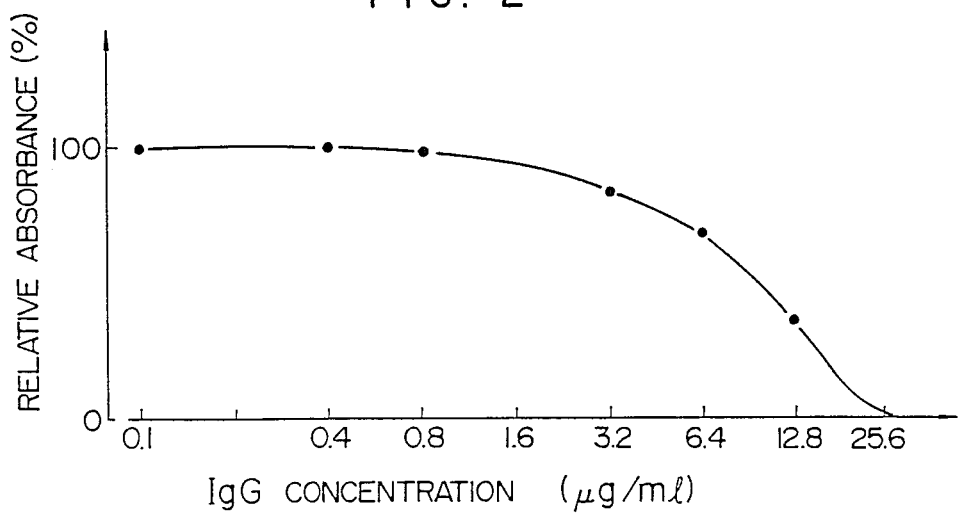
FIG. 2 shows the calibration curve obtained in Referential Example 1; the axis of abscissa refers to IgG concentration ($\mu$g/ml) and the axis of ordinate to relative absorbance (%) determined by taking as 100% that in case where IgG concentration of test sample was zero.

The relationship between IgG concentration (μg/ml) and relative absorbance (%) (a calibration curve) is shown in FIG. 2. In FIG. 2 there was taken as 100% the relative absorbance in case where IgG concentration of test sample was zero. As shown in FIG. 2, there is a good correlation between IgG concentration and relative absorbance, and therefore it can be seen that the IgG-attached liposomes obtained in Example 11 are suitable for quantitating IgG.

EXAMPLE 12

Preparation of LPS-liposomes having C-reactive protein (CRP) attached thereto

One-quarter of the LPS-liposome dispersion obtained in Example 2 was mixed with 3 mg of SPDP-modified CRP obtained in the same manner as for the SPDP-modified IgG of Example 11, and the resulting mixture was subjected to reaction overnight at room temperature. After completion of the reaction, the supernatant was removed by ultra-centrifugation (34,000 r.p.m., 75,000 xg) and the pellet was re-dispersed into HEPES buffer to obtain a CRP-attached LPS-liposome dispersion.

REFERENTIAL EXAMPLE 2

Quantitation of CRP using CRP-attached LPS-liposomes

CRP was quantitated using the CRP-attached LPS-liposomes obtained in Example 12, with the aid of serum complement in the same manner as in Referential Example 1.

Figure 3:
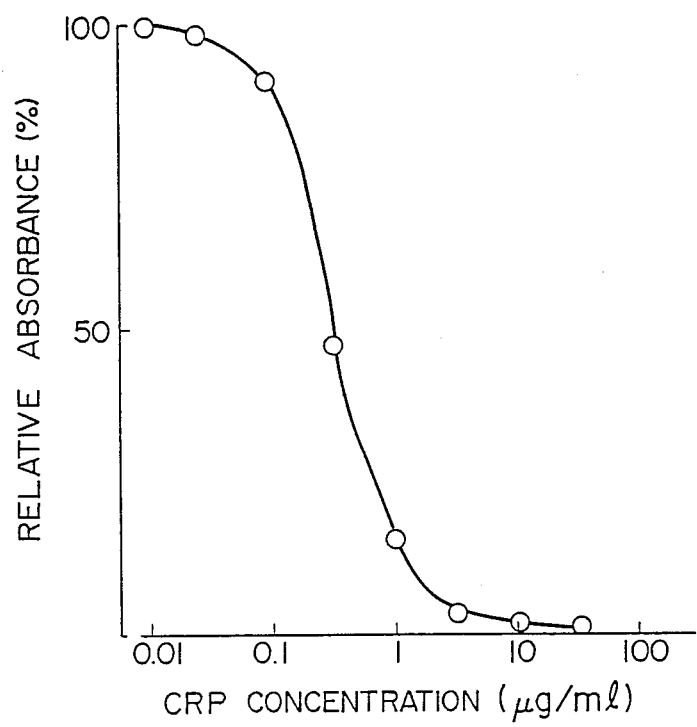
FIG. 3 shows the calibration curve obtained in Referential Example 2; the axis of abscissa refers to CRP concentration ($\mu$g/ml) and the axis of ordinate to relative absorbance (%) determined by taking as 100% that in case where CRP concentration of test sample was zero.

The relationship between the CRP concentration ($\mu$g/ml) and relative absorbance (%) (a calibration curve) is shown in FIG. 3. In FIG. 3 there was taken as 100% the relative absorbance in case where CRP concentration of test sample was zero. It can be seen that as obvious from FIG. 3, the CRP-attached LPS-liposomes obtained in Example 12 is suitable for quantitating CRP.

EXAMPLE 13

Preparation of IgG-attached liposomes (immobilization of IgG using LPS as a spacer)

(1) Preparation of LPS-liposomes

In a test tube were placed 325 $\mu$l of a 20 mM solution of DPPC in chloroform, 325 $\mu$l of a 20 mM solution of cholesterol in chloroform, 85 $\mu$l of a 7.6 mM solution of DPPG in chloroform/methanol (95/5), and a suspension of 2 mg of LPS (molecular weight: about 20,000) in 1 ml of chloroform/methanol (1:1), and after mixing, the solvent was distilled off by means of a rotary evaporator. The residue was dried in a desiccator for 3 hours, after which 0.5 ml each of chloroform and diethyl ether were added, followed by adding thereto 80 $\mu$l of AP solution [a solution of 5,000 unit/2.5 ml of AP mfd. by Sigma Chemical Company in 0.01M HEPES (N-2-hydroxyethylpiperazine-N'-2-ethanesulfonic acid) buffer, pH 7.4], and the resulting mixture was vigorously shaken in a Vortex mixer. The mixture was then concentrated on a water bath (43° to 48° C.) by means of a rotary evaporator, and the organic solvent was removed by distillation, after which 1 ml of 0.01M HEPES buffer was added and the resulting mixture was stirred in a Vortex mixer until uniform dispersion was achieved. The dispersion thus obtained was transferred to a centrifuge tube and centrifuged at 34,000 r.p.m, 75000 xg: at 4° C. for 40 minutes was repeated 5 times to remove the free AP. Then, the residue was suspended in 3 ml of 0.3M sodium bicarbonate buffer (pH 8.2) containing 7.25 mM NaCl, and the resulting suspension was stored at 4° C.

(2) Production of IgG-attached liposomes

A solution of 0.706 mg of sodium metaperiodate in 1 ml of 0.3M sodium bicarbonate buffer (pH 8.2) was added to 1 ml of the liposome suspension obtained in (1) above, after which the resulting mixture was stirred at room temperature for 1 hour and then transferred to a centrifuge tube, and centrifugation at 34,000 r.p.m., 75,000 xg at 4° C. for 40 minutes was repeated twice. In the centrifugation, 0.01M potassium carbonate buffer (pH 9.5) containing 7.25 mM NaCl was used for washing, and finally the pellet thus obtained was suspended in 1 ml of this buffer. A solution of 3 mg of IgG in the same buffer as shown was added and the resulting mixture was stirred at room temperature for 2 hours, after which a solution of 0.6 mg of sodium borohydride in 100 $\mu$l of 0.01M potassium carbonate buffer was added, and the resulting mixture was stirred for another 1 hour. The mixture was then transferred to a centrifuge tube and centrifugation at 34,000 r.p.m. 75,000 xg at 4° C. for 40 minutes was repeated three times. In the centrifugation, 0.01M HEPES buffer was used for washing, and finally the pellet was suspended in 2 ml of this buffer and the resulting suspension was stored at 4° C.

EXAMPLE 14

Three kinds of IgG-attached liposomes were produced according to the method of Example 13, except for varying the amount of LPS introduced into liposomes, the amount of an oxidizing agent NaIO$_4$, and the amount of IgG to be coupled to liposomes.

The amount of IgG attached (measured by the Lowry method) and the retention rate of activity of encapsulated substance (AP) are tabulated in Table 2. In FIG. 4 are shown the results of immunolysis conducted for IgG-attached liposomes in the case of 2 in Table 2 in the presence of complement.

COMPARATIVE EXAMPLE 1

Three kinds of IgG-attached liposomes were produced in exactly the same manner as in Example 14, except that ganglioside (molecular weight: about 2,000), a low-molecular-weight glycolipid was used in place of LPS. The amount of attached IgG and the retention rate of activity of encapsulated substance are tabulated together in Table 2. In FIG. 5 are shown the results of immunolysis conducted for IgG-attached liposomes in the case of 5 in Table 2 in the presence of complement.

The retention rate of AP activity was calculated by determining the encapsulated amounts of AP before and after the attachment of IgG from lysis by a surfactant (Briji 58).

FIG. 4 and FIG. 5 show the manners of change, with the concentration of complement, in the absorbance at 410 nm of p-nitrophenol produced from the substrate p-nitrophenylphosphate depending on the amount of AP released from the IgG-attached liposomes of each kind by their damage which is caused a when various concentrations of complement was allowed to act on the IgG-attached liposomes and b when 500-fold diluted anti-IgG antibody (antiserum) and various concentrations of complement were allowed to act on the IgG-attached liposomes. In FIGS. 4 and 5, the axis of ordinate refers to absorbance at 410 nm and the axis of abscissa to the concentration of complement. The solid line shows the results obtained when the complement alone was allowed to act, and the broken line the results obtained when both the antibody and the complement were allowed to act.

TABLE 2

|  | No. | Using amount of LPS or ganglioside | | Using amount of NaIO4 | Using amount of IgG | Amount of IgG attached | Retention rate of Ap activity |
| --- | --- | --- | --- | --- | --- | --- | --- |
|  | 1 | LPS | 0.67 | 0.33 | 300 | 114 | 61 |
| Example 14 | 2 | LPS | 0.67 | 0.33 | 3,000 | 208 | 83 |
|  | 3 | LPS | 1.34 | 3.3 | 300 | 127 | 70 |
| Comparative | 4 | Ganglioside | 0.067 | 0.33 | 300 | 58 | 29 |
| Example 1 | 5 | Ganglioside | 0.067 | 0.33 | 3,000 | 91 | 29 |
|  | 6 | Ganglioside | 0.134 | 3.3 | 300 | 69 | 45 |

Note 1:
The using amounts of LPS, ganglioside, NaIO4 and IgG and the amount of attached IgG are all expressed in terms of values per 2.2 μmol of DPPC.
Note 2:
The encapsulated amount of AP before the attaching of IgG was 25.7 units for liposomes obtained by using 0.67 mg of LPS, 25.4 units for those obtained by using 1.34 mg of LPS, 14.7 units for those obtained by using 0.067 mg of ganglioside, and 14.9 units for those obtained by using 0.134 mg of ganglioside.

As is evident from Table 2, the liposomes on which IgG was immobilized by the method of this invention using LPS as a spacer have an amount of attached IgG of as high as about 2 times of that of the liposomes on which IgG was immobilized by use of ganglioside, i.e., a low-molecular-weight glycolipid as a spacer [the above-mentioned conventional method (ii)]. The retention rate of activity of encapsulated AP determined by comparison between the encapsulated amounts before and after the immobilizing reaction with IgG is 60 to 80% for the former liposomes, and this value is much higher than a value of about 30 to 45% for the latter liposomes. This fact indicates that damage to liposomes at the time of the immobilizing reaction is much slighter in the case of the method of this invention than in the case of the conventional method.

As is evident from FIG. 4 and FIG. 5, the liposomes on which IgG has been immobilized by the method of this invention (by use of LPS as a spacer) underwent immunolysis apparently, while the liposomes on which IgG has been immobilized using ganglioside, i.e., a low-molecular-weight glycolipid as a spacer did not undergo immunolysis at all.

EXAMPLE 15

Preparation of peptide-attached liposomes
(immobilization using LPS as a spacer)

A solution of 2.14 mg of sodium metaperiodate in 1 ml of 0.3M sodium bicarbonate buffer was added to 2 ml of a liposome (containing 2 mg of LPS having average molecular weight of 20,000) suspension prepared by the REV method, after which the resulting mixture was stirred at room temperature for 1 hour and then transferred to a centrifuge tube, and centrifugation at 34,000 r.p.m. at 4° C. for 40 minutes was repeated twice. In the centrifugation, 0.01M potassium carbonate buffer was used for washing, and finally the pellet was suspended in 2 ml of this buffer. A solution of 3 mg (about 1 μmol) of C-terminal peptides (CTP 118–145) of β-subunit for hCG in 1 ml of said buffer was added, and the resulting mixture was stirred at room temperature for 2 hours, after which a solution of 0.9 mg of sodium borohydride in 100 μl of said buffer was added, and the mixture thus obtained was stirred for another 1 hour. This mixture was then transferred to a centrifuge tube and centrifugation at 34,000 r.p.m. at 4° C. for 40 minutes was repeated three times. In the centrifugation, 0.01M HEPES buffer was used for washing, and finally the pellet was suspended in 2 ml of this buffer and the resulting suspension was stored at 4° C.

The peptide content of the peptide-attached liposomes prepared in the manner described above was determined by a fluorometric method using fluoresamine to find that 9.6 nmol of the peptide had been attached to the liposomes. That is to say, the peptide had been attached in an amount of about 1.5 nmol per μmol of the lipid.

What we claim is:

1. A functionalized liposome comprising at least one phospholipid and an amphiphilic compound selected from the group consisting of natural and synthetic lipopoly saccharides, natural and synthetic polypeptides having hydrophobic substituents and synthetic hydrophilic polymers whose ends have been made hydrophobic, and having a molecular weight of about 5,000 to about 30,000.

2. A functionalized liposome according to claim 1, wherein the amphiliphilic compound is a natural or synthetic lipopolysaccharide.

3. A functionallized liposome according to claim 2, wherein said synthetic lipopolysaccharide is obtained by chemical modification of a naturally occurring lipopolysaccharide.

4. A functionalized liposome according to claim 1, wherein the amphiphilic compound is present in an amount of 0.01 to 2 w/w % based upon the amount of phospholipid.

5. A functionallized liposome according to claim 1, further comprising an agent selected from the group consisting of immunological substances, physiologically active substances and pharmaceuticals.

6. A functionallized liposome according to claim 5, wherein said agent is at least one member selected from the group consisting of enzymes, complete genes, polynucleotides, hormones and immunoglobulins.

7. A functionalized liposome according to claim 5, wherein said agent is at least one member selected from the group consisting of drugs, anitbiotics, dyes, fluorescent substances and luminous compounds.

8. A functionallized liposome according to claim 1, which has an immunological substance or a physiologically active substance immobilized thereon.

9. A functionalized liposome according to claim 8, which has an immunological substance or a physiologically active substance immobilized thereon through the amphiphilic compound having a molecular weight of about 5,000 to about 30,000.

10. A functionallized liposome according to claim 9, wherein the amphiphilic compound is at least one member selected form the group consisting of natural and synthetic lipopolysaccharides, natural and synthetic polypeptides having a hydrophobic group and synthetic hydrophilic polymers whose ends have been made hydrophobic.

11. A functionallized liposome according to claim 8, wherein the immunological substance is selected form the group consisting of low-molecular weight antigens, haptens and antibodies thereto.

12. The functionallized liposome according to claim 8, wherein the physiologically active substance is selected from the group consisting of hormones and physiologically active chemical compositions.

13. A process for producing functionallized liposomes, characterized by forming functionallized liposomes in the presence of an amphiphilic compound selected from the group consisting of natural and synthetic lipopoly saccharides, natural and synthetic polypeptides having hydrophobic substituents and synthetic hydrophilic polymers whose ends have been made hydrophobic, and having a molecular weight of about 5,000 to about 30,000.

14. A process according to claim 13, wherein said liposomes are formed in the presence of an amphiphilic compound having a molecular weight of about 5,000 to 30,000 by a method selected from the group consisting of vortexing, sonication, surfactant, treatment reverse-phase evaporation (REV), prevesicle, French press extrusion, $Ca^{2+}$ fusion, annealing, freeze-thaw, w/o/w emulsion and stable plurimellar vesicle.

15. The process according to claim 13, which comprises forming liposomes, and further immobilizing thereon an immunological substance or a physiologically active substance.

16. The process according to claim 13, which comprises immobilizing an immunological substance or a physiologically active substance on liposomes through an amphiliphilic compound having a molecular weight of about 5,000 to about 30,000 introduced into the liposomes as a part of matrix material.

17. The process according to claim 16, wherein the immobilization is carried out by activating the hydrophilic portion of the amphiphilic compound or by using a cross-linking agent or a condensing agent.

* * * * *